United States Patent [19]

Higashiyama et al.

(10) Patent No.: US 7,498,127 B2
(45) Date of Patent: Mar. 3, 2009

(54) METHOD OF SCREENING CELL GROWTH INHIBITOR AND CELL GROWTH INHIBITOR (76) Inventors: Shigeki Higashiyama, 357-6, Yokogawara, Shigenobu-cho, Onsen-gun, Ehime 791-0203 (JP); Daisuke Nanba, Daisan-copo yamato 205, Hinokuchi 1406, Shibenobu-cho, Onsen-gun Ehime 791-0202 (JP)

( * ) Notice: Subject to any disclaimer, the term of this patent is extended or adjusted under 35 U.S.C. 154(b) by 176 days.

(21) Appl. No.: 10/506,049

(22) PCT Filed: Dec. 19, 2003

(86) PCT No.: PCT/JP03/16410

§ 371 (c)(1), (2), (4) Date: Aug. 30, 2004

(87) PCT Pub. No.: WO2004/057330

PCT Pub. Date: Jul. 8, 2004

(65) Prior Publication Data

US 2005/0255443 A1 Nov. 17, 2005

(30) Foreign Application Priority Data

Dec. 20, 2002 (JP) .............................. 2002-369524
Nov. 7, 2003 (JP) .............................. 2003-379214

(51) Int. Cl.
C12Q 1/00 (2006.01)
C07H 21/04 (2006.01)
C12P 21/06 (2006.01)
C12N 15/09 (2006.01)
C07K 14/475 (2006.01)

(52) U.S. Cl. ................... 435/4; 435/69.1; 435/320.1; 435/325; 530/350; 536/23.5

(58) Field of Classification Search ...................... None
See application file for complete search history.

(56) References Cited

U.S. PATENT DOCUMENTS 5,811,393 A * 9/1998 Klagsbrun et al. ............ 514/12
6,638,543 B2 * 10/2003 Kang et al. ................. 424/757
7,045,311 B2 * 5/2006 Ciambrone et al. ........... 435/23

FOREIGN PATENT DOCUMENTS

EP 0 867 505 9/1998

(Continued)

OTHER PUBLICATIONS

Prenzel et al., Nature. Dec. 23, 1999; 402:884-888.*

(Continued)

*Primary Examiner*—Gary B Nickol
*Assistant Examiner*—Cherie Woodward
(74) *Attorney, Agent, or Firm*—Westerman, Hattori, Daniels & Adrian, LLP.

(57) ABSTRACT

The present invention provides a method for screening a cytostatic agent characterized by determining an effect of inhibiting intracellular signaling mediated by a remaining fragment of a cell membrane-anchored growth factor, and the cytostatic agent. In growth factors of the EGF family, the physiological significance of the remaining fragment is clarified, and a method for controlling its action is searched, and thus a novel pharmaceutical can be provided.

10 Claims, 4 Drawing Sheets

FOREIGN PATENT DOCUMENTS

WO    WO 03012441 A1 *  2/2003

OTHER PUBLICATIONS

Nanba et al., J Cell Biol. Nov. 10, 2003;163(3):489-502. Epub Nov. 3, 2003.*
Asakura et al., Nat Med. Jan. 2002;8(1):35-40.*
Hirata et al., Biochem Biophys Res Commun. May 18, 2001;283(4):915-22, abstract only.*
Shakovitch et al., Mol Cell Biol. Sep. 1998;18(9):5533-5545.*
UniProt Accession No. Q05516 (ZBT16_human, also called zinc finger protein PLZF, PLZF protein, and zinc finger and BTB domain-containing protein Nov. 16, 1995).*
Jans. FASEB J. Aug. 1994;8(11):841-7. Review.*
Iwamoto et al. Cytokine Growth Factor Rev. Dec. 2000;11(4):335-44. Review.*
Adam et al. Cancer Research. Jan. 15, 2003;63:484-490.*
Bao et al. Cell Biol. Jun. 23, 2003;161(6):1133-41.*
Davis Fleisher et al. Front Biosci. Mar. 1, 1998;3:d288-99. Review.*
American Heritage Dictionary. 2000. Houghton-Mifflin Co.—Cytostatic.*
Nanba et al.; The Journal of Cell Biology, vol. 163, No. 3, pp. 1-14, (2003) Cited in the PCT search report.
Bochen Pan et al., "The soluble and membrane-anchored forms of heparin-binding epidermal growth factor-like growth factor appear to play opposing roles in the survival and apoptosis of human luteinized granulose cells", *Molecular Human Reproduction* vol. 8, No. 8, pp. 734-741, Aug. 2002, European Society of Human Reproduction and Embryology.
Seung Hyum Han et al., "VDUPI upregulated by TGF-β1 and 1,25-dihydorzyvitamin $D_3$ inhibits tumor cell growth by blocking cell-cycle progression", *Oncogene*, vol. 22, No. 26, pp. 4035-4046, Jun. 26, 2003, Nature Publishing Group.

* cited by examiner

METHOD OF SCREENING CELL GROWTH INHIBITOR AND CELL GROWTH INHIBITOR

TECHNICAL FIELD

The present invention relates to a method for screening a cytostatic agent capable of inhibiting an intracellular signaling process that has not been conventionally known. The method of the present invention is significantly useful as a method for screening cytostatic agents, in particular, antitumor agents, antirheumatic agents, agents for treating cardiac disorder, etc. that are based on a novel action mechanism.

BACKGROUND ART

A large number of cell membrane-anchored growth factors that are synthesized in vivo as a cell membrane-anchored precursor, become soluble in response to cleavage by a processing enzyme (shedding) and express their actions are known.

For example, a heparin-binding EGF-like growth factor (HB-EGF), amphiregulin, epiregulin, transforming growth factor-α (TGF-α) and the like are members of the epidermal growth factor (EGF) family, and it has been clarified that all of the growth factors that belong to the EGF family are biosynthesized as a cell membrane-anchored precursor and become soluble in response to processing. It is known that in general, the solubilized growth factor is then bound to a receptor of the ErbB receptor family in an activated form so as to express the action of a growth factor.

It is known that similarly to these growth factors of the EGF family, tumor necrosis factors (TNF-α) express a large number of physiological actions in an activated form after the cell membrane-anchored precursor has been subjected to processing by proteases.

However, in any case, the role of a fragment that is left in the cell surface (hereinafter, referred to as "remaining fragment") after the activated form is released by processing has not been known.

On the other hand, the mechanism in which a membrane-anchored receptor releases a signal transducer (second messenger) in response to extracellular stimulations and transduces external signals to a cell is well known. In recent years, a signaling mechanism (regulated intramembrane proteolysis; RIP) has been presented and gained much attention, in which processing of an extracellular domain of a membrane-anchored protein causes a remaining fragment to be translocated into the nucleus, after being subjected to further processing in some cases, and to regulate the transcription of a gene (M. S. Brown et al., Cell, 100, 391-396(2000)).

However, in this as well, only the fact of signaling into the nucleus has been identified, but the meaning of the signal, and the physiological significance such as the subsequent phenomenon caused by the transduced signals have not been clarified yet.

Furthermore, at least regarding HB-EGF, the behavior itself of the remaining fragment after processing has not been known at all Cell, 100, 391-396 (2000) (M. S. Brown et al.)

DISCLOSURE OF INVENTION

In the growth factors of the EGF family including HB-EGF, the physiological significance of the remaining fragment is not known at all. It is an object of the present invention to identify its physiological significance and to provide a novel method for regulating its action, and a novel pharmaceutical.

Among a variety of membrane-anchored growth factors, the inventors of the present invention focus particularly on HB-EGF and transfected HB-EGF whose carboxy-terminal (C terminal) in the intracellular domain is modified with a fluorescence into a cell for the purpose of tracing the remaining fragment. Then, the manner in which after the extracellular domain of the HB-EGF is subjected to processing by a solubilizing enzyme, the tagged intracellular domains accumulate around the nucleus was observed under a microscope.

Since the transport of the remaining fragment into the nucleus was suggested, then an intranuclear protein that interacts with the remaining fragment of the HB-EGF was searched. As a result of searching a human heart cDNA library with a system employing a yeast (two-hybrid system; Clontech), using the intracellular domain (185-208aa) of the HB-EGF as bait, promyelocytic leukemia zinc finger (hereinafter, referred to as PLZF) protein was found out as a protein that interacts therewith.

It is known that the PLZF protein suppresses the cell growth by suppressing the action of cyclin A in the cell nucleus (Yeyati et al., Oncogene, 18, 925-934(1999)). Therefore, it was suggested that the remaining fragment of the HB-EGF might participate in the control of cell growth by interacting with the PLZF protein.

As a result of in-depth research, the inventors of the present invention found out the following facts.

1) In the cells in which a tagged PLZF protein is transfected into its nucleus, when the extracellular domain of the HB-EGF is subjected to processing by a solubilizing enzyme, the remaining fragment is bound to a region including $C_2H_2Zn$ finger motifs of the tagged PLZF protein.

2) The nuclear export of the tagged PLZF protein is observed.

3) Cyclin A is expressed in the nucleus in response to the nuclear export of the tagged PLZF protein.

4) With the expression of cyclin A, a reduction in the amount of internalized bromodeoxyuridine (BrdU) is observed, and the progression of the cell cycle is seen.

Then, the fact that the nuclear export described in 2) is inhibited by the addition of an antitumor agent reptomycin B (see the example below) was confirmed, and thus the present invention has been achieved.

Hereinafter, the present invention will be described in detail.

BEST MODE FOR CARRYING OUT THE INVENTION

"Screening" referred to in the present invention includes not only so-called first screening for selecting the inhibitor of the present invention among a plurality of candidates, but also secondary screening (confirmation test) for confirming the antitumor action (cytostatic ability) of a test substance.

In the present invention, a method for determining an effect of inhibiting intracellular signaling substantially contains the steps of, for each of the cases in the presence and the absence of a test substance, (1) producing a remaining fragment of a cell membrane-anchored growth factor by processing of the growth factor, and (2) determining the extent of the nuclear export of a tagged transcriptional regulator.

The cell membrane-anchored growth factor refers to a growth factor whose precursor is present on the surface of a cell membrane (ectodomain region) and that is known to exert an action by becoming soluble in response to cleavage with a processing enzyme (shedding). For example, the cell membrane-anchored growth factor includes the epidermal growth factor family (EGF family) including epiregulin, amphiregulin, transforming growth factor-α (TGF-α), neuregulin, and NTAK, in addition to HB-EGF.

In the present specification, the remaining fragment includes the following (X), (Y) and (Z).
(X) Fragment that remains after the activated form is released by processing.
(Y) Fragment in which at least a portion of the domain inside the cell membrane of (X) is cleaved by further processing.
(Z) Proteins having the same amino acid sequence as that of (X) or (Y), regardless of the production process.
(Y) tends to be easily freed from a cell membrane by further processing.

The transcriptional regulator refers to a protein (repressor) that inhibits the action of RNA polymerase by binding to a promoter portion of DNA so as to regulate gene expression, and receives signaling by the remaining fragment of the cell membrane-anchored growth factor. The transcriptional regulator includes histone deacetylase (HDAC) such as HDAC5, HDAC7, and HDAC9 and splicing isoform thereof, proteins having BTB/$C_2H_2$Zn finger motifs, and the like. Specific examples of the proteins having BTB/$C_2H_2$Zn finger motifs include PLZF proteins, Bcl-6 proteins, myoneurin proteins, and KIAA0441 ("Kazusa DNA Research Institute" code number) proteins.

Any cell can be used as a test cell, as long as it expresses a growth factor targeted by processing. However, in order to analyze the effect of a specific remaining fragment on signaling, it is preferable to simplify a screening system and use a cell that has expressed only a specific growth factor. For example, in the case of HB-EGF, human fibrosarcoma HT1080 cells to which HB-EGF has been transfected (H1080/HB-EGF) can be used preferably.

In the present invention, not only a wild-type HB-EGF, but also HB-EGF with partial deletion, substitution or addition of the amino acids that does not impair the interaction activity with the intranuclear transcriptional regulator can be used.

For example, the inventors of the present invention confirmed that even if HB-EGF with deletion of 10 amino acids in the C-terminal is used, remaining fragments accumulate around the nucleus, and that in response to processing, the nuclear export of the intranuclear PLZF protein occurs. The inventors of the present invention further confirmed that the substitution of amino acids having charges in the remaining fragment prevents the nuclear exports.

This suggests that the main active portion of the HB-LGF for the nuclear export of the PLZF protein is present in a portion of the amino acid sequence from the $185^{th}$ to $198^{th}$ amino acids (SEQ. ID. NO:4) and that the presence of amino acid residues having positive charges or negative charges is essential for the nuclear export.

Therefore, deleted or substituted-type HB-EGF in which the nuclear export of the PLZF protein can occur is the following (1) or (2), for example.
(1) Deleted-type HB-EGF in which at least one of the amino acids corresponding to an amino acid sequence portion with 10 amino acids from the $199^{th}$ to amino acids (SEQ. ID. NO:5) in the so-called cyto region (cytoplasmic domain), that is, an amino acid sequence portion with 24 amino acids from the $185^{th}$ to $208^{th}$ amino acids (more specifically, RYHRRGGYDVENEEKVKLGMTNSH (SEQ. ID. NO:1)).
(2) Substituted-type HB-EGF in which in the portion after the $185^{th}$ amino acid of the amino acid sequence of wild-type HB-EGF or HB-EGF described in (1), a non-charged amino acid residue is substituted with another non-charged amino acid residue.

Therefore, a method for producing a cytostatic agent of the present invention can be achieved by screening a substance that is bound to an amino acid sequence portion with 14 amino acids of the $185^{th}$ to $198^{th}$ amino acids (SEQ. ID. NO:4) from the amino terminal of a heparin-binding LGF-like growth factor.

In the screening method of the present invention, when performing processing a cell membrane-anchored growth factor, it is common to add an activator of protein kinase C such as 12-O-tetradecanoylphorbol-13-acetate (TPA) to activate a processing enzyme (ADAM12 in the case of HT1080).

It is possible to confirm progression of processing, that is, production of remaining fragments or tagged remaining fragments by identifying the resultant solubilized growth factor.

As a method for identifying production of a solubilized growth factor, the following method can be used, for example, in the case of HB-EGF.

(Method of Using a Transfectant of Alkaline Phosphatase (AP))

Production of solubilized HB-EGF can be confirmed by determining the AP activity according to the method described in a PCT publication (WO01/70269).

(Precipitation Method Using Heparin-beads)

NaCl is added to 1 ml of a culture supernatant such that the concentration of NaCl is 0.35 mols. Then, 20 μl of heparin-sepharose (heparin-beads) is added thereto, and incubated at room temperature for 30 min. Then, the heparin-beads are washed with PBS three times, suspended in 0.5 ml of PBS, reacted with a HB-EGF antibody #H6 (antibody against soluble HB-EGF), and reacted with AP-binding secondary antibody, and thus the AP activity is determined.

(Sandwich ELISA Method Using Diphteria Toxin and HB-EGF Antibody #H6)

Diphteria toxin (manufactured by Sigma) is turned into a solid phase with 3 μg/ml of PBS in 100 μl /well in a 96-well immunoplate. A cell culture supernatant is added in an amount of 100 μl thereto and reacted at room temperature for 2 hours, followed by reaction with biotin-tagged primary antibody, and AP-tagged streptavidin, and thus the AP activity is detected. The plate is washed with PBS/Tween (0.05%) after every reaction.

It should be noted that for processing, endocerine-1 or the like can be used in place of TPA.

The processing process can be varied with the test cell, but generally takes 30 to 90 min in the case of using TPA and takes about one to two hours in the case of using endocerine-1.

After the processing process ends, the procedure goes to the processes for detecting or quantitatively determining of the tagged transcriptional regulator.

Hereinafter, the processes for detecting or quantitatively determining of the tagged transcriptional regulator will be described by taking the PLZF protein as an example.

The PLZF protein can be tagged with a fluorescent protein such as a yellow fluorescent protein (YFP), a cyan fluorescent protein (CFP), and a green fluorescent protein (GFP) e.g., the proteins sold under the trademark LIVING COLORS by Clontech of California, USA) as a fluorescent tag. Alternatively, a highly antigenic synthetic peptide such as synthetic octapeptide (e.g., the peptide sold under the trademark FLAG by Sigma-Aldrich Co. of Missouri, USA) is used as a tag for the PLZF protein, and the tag is detected using, for example, an antibody to which a fluorescent tag such as a fluorescent protein or a coloring matter is bound.

The nuclear export of the PLZF protein is evaluated after the processing process ended and a predetermined time has passed.

More specifically, a tagged protein (CFP-PLZF) obtained by binding, for example, a cyan fluorescent protein (CFP) to the N terminal of the PLZF protein is internalized in a plasmid, and the plasmid is transfected into a test cell by an ordinary method. Then, after a processing process, the extent of the nuclear export is evaluated with a fluorescent microscope (e.g.,a microscope sold under the trademarks ECLIPSE TE300, ZEISS LSM 510 or the like by Nikon Corporation of Japan).

The extent of the nuclear export can be determined by, for example, detecting or quantitatively determining either the tagged transcriptional regulators that remain in the nucleus or the tagged transcriptional regulators that are transported from the nucleus. For example, in the case of detecting or quantitatively determining the tagged transcriptional regulators that remain in the nucleus, the number of the cells in which the nuclear export of the tagged PLZF protein does not occur is counted, and the ratio thereof to the number of the transfectant cells is calculated. Alternatively, the inhibitory effect on the nuclear exports of the PLZF protein of a substance to be tested is evaluated by measuring the fluorescence intensity derived from the tagged PLZF protein in the nucleus and comparing the same with that of the control transfectants.

The method for determining the extent of the nuclear export referred to in the present invention includes a method for determining the extend of the translocation of the tagged transcriptional regulator to the vicinity of the nuclear membrane, which is a pre-stage of the nuclear export.

Furthermore, as described above, it is observed that in the cell transfected with HB-EGF that is modified with a fluorescence in the C terminal in the intracellular domain, when the extracellular domain of the HB-EGF is subjected to processing by a solubilizing enzyme, the tagged substances accumulate around the nucleus in the cell after having approached a golgi apparatus.

Therefore, in the present invention, another method for determining the effect of inhibiting intracellular signaling includes the step of determining the effect of inhibiting signaling from a remaining fragment to an intranuclear transcriptional regulator, instead of the step of determining the extent of the nuclear export of a tagged transcriptional regulator.

Specific examples of the signaling from a remaining fragment to an intranuclear transcriptional regulator includes approach of a remaining fragment to a golgi apparatus, separation afterwards, accumulation around the nucleus, transport into the nucleus, or binding or approach to an intranuclear transcriptional regulator, interaction with an intranuclear transcriptional regulator, formation of a complex of a remaining fragment, an intranuclear transcriptional regulator and DNA, and the like.

The inventors of the present invention clarified that when the transcriptional regulator is a protein having $BTB/C_2H_2Zn$ finger motifs, the approach of the remaining fragment to the intranuclear transcriptional regulator or interaction therebetween occurs between the remaining fragment and the Zn finger region of the protein.

Therefore, one form of the signaling from a remaining fragment to an intranuclear transcriptional regulator in the screening method of the present invention is signaling mediated by the Zn finger region of an intranuclear transcriptional regulator.

Therefore, the method for producing a cytostatic agent of the present invention can be achieved by using a substance bound to the Zn finger region of a protein having BTB/$C_2H_2$Zn finger motifs, or a substance bound to a binding region to a protein having BTB/$C_2H_2$Zn finger motifs in the remaining fragment of a cell membrane-anchored growth factor as an active component. For example, an antibody against the Zn finger region or an antibody against the remaining fragment of a cell membrane-anchored growth factor can be used as active components for the production.

The Zn finger region refers to a region including $C_2H_2$Zn finger motifs. More specifically, it refers to a region including the following 1) and 2).

1) Two $C_2H_2$Zn finger motifs
2) A region having a TGEKPY (SEQ ID NO:2) sequence that couples the two finger motifs described in 1)

More specifically, when the protein having BTB/$C_2H_2$Zn finger motifs is a PLZF protein, the remaining fragment is bound to Zn6 and Zn7, which are the sixth and the seventh finger motifs, respectively, of nine Zn finger motifs and the TGEKPY (SEQ ID NO:2) sequence that is sandwiched therebetween. However, only the region of Zn6 to Zn7 is insufficient for binding, and the region of Zn5 to Zn8 is necessary, as shown in Test Example 1 below.

When the protein having BTB/$C_2H_2$Zn finger motifs is a Bcl-6 protein, the remaining fragment is bound to Zn4 and Zn5, which are the fourth and the fifth finger motifs, respectively, of six Zn finger motifs and the TGEKPYP (SEQ ID NO:3) sequence (Zn4 to Zn5) that is sandwiched therebetween.

When the protein having BTB/$C_2H_2$Zn finger motifs is a myoneurin protein, the remaining fragment is bound to Zn5 and Zn6, which are the fifth and the sixth finger motifs, respectively, of eight Zn finger motifs and the TGEKPY (SEQ ID NO:2) sequence (Zn5 to Zn6) that is sandwiched therebetween.

The tendency of the accumulation around the nucleus or the nuclear import of the tagged substance can be evaluated in the same manner as described above, that is, by counting the number of transfectant cells in which the accumulation does not occur, or measuring the fluorescence intensity derived from the tagged substance around or in the cell.

When a protein that is a remaining fragment artificially produced by another method than processing is used as a protein for screening a cytostatic agent, an NLS (nuclear localization signal) protein as a membrane-anchored factor can be bound to the fragment. Therefore, a gene encoding the amino acid sequence of this protein for screening is useful for producing this protein that is can be used for screening kit.

The site to be tagged NLS in this case is not necessarily an amino acid in the C terminal, but can be any site, as long as the signaling is not affected.

The cytostatic agent selected by the screening method of the present invention is a substance that inhibits signaling in the cell mediated by the remaining fragment of a cell membrane-anchored growth factor, and examples of the candidates can include the following:

(I) One of the candidates is a substance that acts on a region interacting with a remaining fragment (b) in a transcriptional regulator (a).

More specifically, the substance can be a protein that has the same or a similar structure to the remaining fragment and that antagonizes the original remaining fragment and inhibits the signaling of the remaining fragment.

When this protein having a structure similar to that of the remaining fragment is used as a cytostatic agent, in order to increase the antagonist properties against the original remaining fragment, it is preferable to transfect the protein into a cell in a higher concentration than that of an endogenous cell membrane-anchored growth factor.

In addition, for example, the following substance can be used, and it can be used as a single substance or in the form of an aggregate of a plurality of substances.

When the transcriptional regulator (a) is a protein having BTB/$C_2H_2$Zn finger motifs, a substance inhibiting intracellular signaling mediated by the remaining fragment (b) is a substance that is bound to or approaches the Zn finger region of the protein, which is a region that interacts with (b) in (a), and inhibits the interaction between the Zn finger region and the remaining fragment.

More specifically, it is a substance that is bound to or approaches at least one site of the two motifs described in 1) and the region described in 2), but preferably is bound to or approaches two sites. This binding or approach is not necessarily throughout each region, but can be in such an extent that the remaining fragment can be substantially inhibited from being bound to or approaching the region.

1) Two $C_2H_2$Zn finger motifs
2) A region having a TGEKPY (SEQ ID NO:2) sequence that couples the two finger motifs described in 1)

When the protein having BTB/$C_2H_2$Zn finger motifs is a PLZF protein, the two $C_2H_2$Zn finger motifs referred to in 1) correspond to at least two of the fifth to the eighth Zn finger motifs, that is, Zn5 to Zn8, of nine Zn finger motifs. The region referred to in 2) corresponds to the TGEKPY (SEQ ID NO:2) sequence between Zn6 and Zn7 (Test Example 1).

When the protein having BTB/$C_2H_2$Zn finger motifs is a Bcl-6 protein, the two $C_2H_2$Zn finger motifs referred to in 1) correspond to the fourth and the fifth Zn finger motifs, that is, Zn4 and Zn5, of six Zn finger motifs. The region referred to in 2) corresponds to the TGEKPYP (SEQ ID NO:3) sequence (Test Example 2).

When the protein having BTB/$C_2H_2$Zn finger motifs is a myoneurin protein, the two $C_2H_2$Zn finger motifs referred to in 1) correspond to the fifth and the sixth Zn finger motifs, that is, Zn5 and Zn6, of the eight Zn finger motifs. The region referred to in 2) corresponds to the TGEKPY (SEQ ID NO:2) sequence.

As the substance that is bound to or approaches at least one site of the regions including 1) and 2), pseudo-peptide or a pseudo-synthetic compound of the remaining fragment of the EGF family protein, or antibodies against the region including 1) and 2) can be used.

The antibodies against the region including 1) and 2) can be produced by an ordinary method in which mice or the like are immunized, using at least one site of the two motifs described in 1) and the region described in 2) as an antigen. However, in order to inhibit signaling more reliably, a combination of antibodies against two respective sites as an antigen or an antibody that can recognize the two sites at one time is preferable.

(II) Another substance that inhibits intracellular signaling mediated by the remaining fragment is a substance that acts on a region interacting with (a) in (b).

More specifically, the substance can be an antibody against the remaining fragment (b) or a protein having the same or a similar structure to the intranuclear transcriptional regulator (a), and these substances antagonize the original intracellular transcriptional regulator (a) and inhibit the signaling into the intracellular transcriptional regulator.

When this protein having a structure similar to that of the intracellular transcriptional regulator (a) is used as a cytostatic agent, in order to increase the antagonist properties against the original intracellular transcriptional regulator (a), it is preferable to transfect the protein into a cell in a higher concentration than that of an endogenous intracellular transcriptional regulator (a).

When the transcriptional regulator (a) is a protein having BTB/$C_2H_2$Zn finger motifs, a substance inhibiting intracellular signaling mediated by the remaining fragment (b) is a substance that acts on a region interacting with the Zn finger region of the protein, which is a region that interacts with (a) in (b), and inhibits the interaction between the Zn finger region and the remaining fragment.

More specifically, it is a substance that antagonizes the intranuclear transcriptional regulator (a) and acts on a region in (b) with which at least one site of the two motifs described in 1) and the region described in 2) in (a) interacts. An antagonizing substance that antagonizes the intranuclear transcriptional regulator (a) in at least two sites is preferable. This interaction is not necessarily performed throughout each region of 1) and 2) in (b), but can be in such an extent that the intranuclear transcriptional regulator (a) can be substantially inhibited from interacting with the region.

1) Two $C_2H_2$Zn finger motifs
2) A region having a TGEKPY (SEQ ID NO:2) sequence that couples the two finger motifs described in 1)

As the substance that interacts with at least one site of the regions including 1) and 2), pseudo-peptide or a pseudo-synthetic compound of at least a portion of the Zn finger region in the intracellular regulator, or antibodies against the region that interacts with the Zn finger region of the intranuclear regulator in the remaining fragment can be used.

These antibodies also can be produced by an ordinary method in which mice or the like are immunized, using at least a portion of the region that interacts with the Zn finger region of the intranuclear regulator (a) in the remaining fragment as an antigen. However, in order to inhibit signaling more reliably, it is preferable to use an antibody that can recognize as many regions as possible of the regions that interacts with the Zn finger region.

The inventors of the present invention confirmed that the nuclear export of PLZF is inhibited by a "rabbit polyclonal antibody using a remaining fragment of HB-EGF as an antigen".

When the remaining fragment (b) is a remaining fragment of HB-EGF, an antibody against at least a portion of the sequence of 14 amino acids from the 185$^{th}$ to 198$^{th}$ amino acids (SEQ ID NO:4) from the amino terminal of HB-EGF before processing, which is a region that interacts with the intranuclear regulator (a), can be used.

These antibodies also can be produced by an ordinary method in which mice or the like are immunized, using at least a portion of the sequence of 14 amino acids from the 185$^{th}$ to 198$^{th}$ amino acids (SEQ ID NO:4) as an antigen. However, in order to inhibit signaling more reliably, it is preferable to use an antibody against as many amino acid portions as possible of the amino acid sequence from the 185$^{th}$ to 198$^{th}$ amino acids (SEQ ID NO:4).

Another example of the substance inhibiting intracellular signaling mediated by the remaining fragment of a cell membrane-anchored growth factor can be a substance inhibiting the intranuclear transcriptional regulator from being transported from the nuclear. Specific examples thereof include a substance inhibiting interaction between the intranuclear transcriptional regulator and exportin such as reptomycin B, which inhibits the binding or approach of a PLZF protein to CRM1 or the like, which is an exportin involved in the nuclear export thereof.

These cytostatic agents of the present invention can be used to treat diseases caused by cell growth.

TEST EXAMPLE 1

Binding Region of HB-EGF Remaining Fragment with Respect to PLZF Protein

1. Test Method (1) In order to specify a region of PLZF protein that interacts with a remaining fragment, GST pull-down assay was performed.

(2) GST, GST binding HB-LGF remaining fragments that were expressed and isolated with *E. coli* BL21 strain according to the GST pull-down assay standard protocol were used. The fragments were bound to Glutathione Sepharose beads, and then cell lysates containing various FLAG-tagged PLZF protein derivatives were incubated with 20 .mu.l of the beads at 4.degree. C. for two hours. After washing with water, the bound protein was analyzed by immunoblotting using anti-FLAG antibody (referring to the peptide sold under the trademark FLAG by Sigma Aldrich Co.).

2. Test Results

The remaining fragments of HB-EGF were bound to the following PLZF protein derivatives as firmly as the wild-type PLZF.
1) Derivatives consisting only of a region of Zn1 to Zn9 of the PLZF protein
2) Derivatives consisting only of a region of Zn4 to Zn9 of the PLZF protein
3) Derivatives consisting only of a region of Zn5 to Zn8 of the PLZF protein The remaining fragments of HB-EGF were bound to the following PLZF protein derivatives, although not so firmly as the wild-type PLZF.
4) Derivatives consisting only of a region of Zn1 to Zn6 of the PLZF protein On the other hand, the remaining fragments of HB-EGF were not bound to the following PLZF protein derivatives.
5) Derivatives with deletion of the Zn finger region of the PLZF protein
6) Derivatives consisting only of the BTB region of the PLZF protein
7) Derivatives consisting only of a region of Zn6 to Zn7 of the PLZF protein
8) Derivatives with deletion of a region of Zn6 to Zn7 of the PLZF protein The results above indicate that the region of Zn5 to Zn8 covering the region Zn6 to Zn7 is necessary.

TEST EXAMPLE 2

Binding Region of HB-EGF Remaining Fragment with Respect to Bcl-6 Protein

1. Test Method

The binding region of HB-EGF remaining fragments with respect to Bcl-6 protein was investigated in the same method as in Test Example 1

2. Test Results

The remaining fragments of HB-EGF were bound firmly to the following Bcl-6 protein derivatives.
1) Derivatives consisting only of a region of Zn1 to Zn6 of the Bcl-6 protein 2) Derivatives consisting only of a region of Zn1 to Zn5 of the Bcl-6 protein
3) Derivatives consisting only of a region of Zn2 to Zn6 of the Bcl-6 protein
4) Derivatives consisting only of a region of Zn3 to Zn6 of the Bcl-6 protein
5) Derivatives consisting only of a region of Zn4 to Zn6 of the Bcl-6 protein The remaining fragments of HB-EGF were bound to the following Bcl-6 protein derivatives, although not so firmly as the above derivatives.
6) Derivatives consisting of Zn1 to Zn4 and a TGEKPY (SEQ ID NO:2) sequence bound to the C terminal of Zn4 of the Bcl-6 protein
7) Derivatives consisting of Zn5 to Zn6 and a TGEKPYP (SEQ ID NO:2) sequence bound to the N terminal of Zn5 of the Bcl-6 protein The remaining fragments of HB-EGF were not bound to the following Bcl-6 protein derivatives.
8) Derivatives consisting only of a region of Zn1 to Zn4 of the Bcl-6 protein
9) Derivatives with delection of a region of Zn1 to Zn3 of the Bcl-6 protein
10) Derivatives with delection of a region of Zn1 to Zn2 of the Bcl-6 protein
11) Derivatives with delection of a region of Zn5 to Zn6 of the Bcl-6 protein The results above indicate that the TGEKPY(P) (SEQ ID NO:2 or SEQ ID NO:3) sequence between Zn4 and Zn5 and at least one region of Zn4 and Zn5 (preferably both) are necessary.

TEST EXAMPLE 3

Nuclear Export of PLZF Protein by Processing

1. Test Method
The following cell groups were used:
1) Human fibrosarcoma HT1080 cells
2) HT1080 cells to which HB-EGF has been transfected (HT1080/HB-EGF)
3) Metalloprotease domain-deleted mutant of ADAM12 in the above cells (HT1080/ΔMP-ADAM12/HB-EGF)
4) HT1080 cells to which processing resistant HB-EGF has been transfected (HT1080/HB-EGF-UC)

1) to 3) already have been reported (Asakura et al., Nat. Med., 8, 35-40 (2002))
44) was produced by transfecting an expression vector of processing resistant (uncleavable) HB-LGF (Hirata et al., BBRC, 283, 915-922 (2001)) into HT1080 cells using LIPO-FECTAMTNE 2000 reagent (sold by Invitrogen of California, USA).

The PLZF protein was tagged by transfecting cDNA of a cyan fluorescent protein (CFP) into the N-terminal side of CDNA of the PLZF protein, and the tagged CDNA of the PLZF protein was transfected into each cell utilizing a commercially available vector (pECFP-C1; Clontech).

Each transfectant containing CFP-PLZF was cultured for 24 hours, and then 100 nM TPA was added thereto for treatment for 60 min. The number (N) of the cells expressing CFP-PLZF in the nucleus and the number (C) of the cells in which CFP-PLZF has leaked into the cytoplasm are counted under observation with a fluorescent microscope before and after the TPA treatment, and the ratio of the number (N) of the cells expressing CFP-PLZF in the nucleus to the total number (N+C) of the cells expressing CFP-PLZF is calculated and thus obtained (N/(N+C)×100 (%)). The wild-type HT1080 cells (the above described 1)) were used as the control for comparison.

Figure 1:
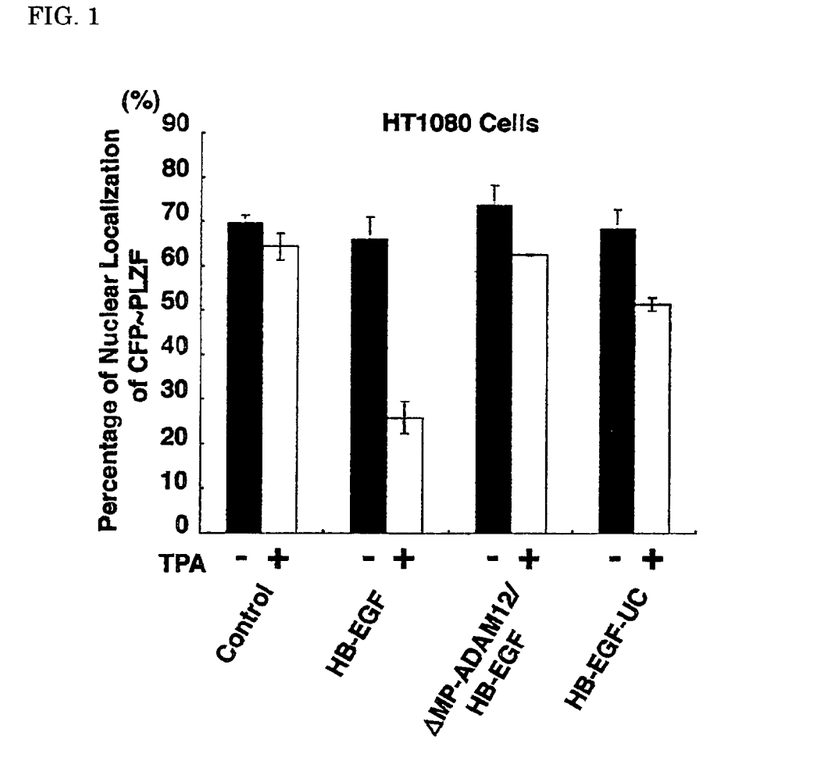
FIG. 1 is a graph showing the nuclear export effect of an intranuclear PLZF protein by processing. The vertical axis shows the ratio (%) of the number of cells expressing CFP-PLZF in the nucleus with compared to the total number of the CFP-PLZF transfectant cells. The colored bar graph shows the results without TPA treatment, and the colorless bar graph shows the results with TPA treatment. The horizontal axis shows HB1080, HB1080/HB-EGF, HT1080/ΔMP-ADAM12/HB-EGF, and HT1080/HB-EGF-UC respectively.

2. Test Results
FIG. 1 shows the results. The TPA treatment triggered processing, and the remaining fragment of HB-EGF caused the nuclear export of the PLZF protein present in the nucleus of the cell. As a result, in HT1080/HB-EGF, the TPA treatment reduced the fluorescence intensity of CFP-PLZF present in the nucleus, whereas in the control cells (HT1080) in which HB-EGF is not present, the fluorescence intensity of CFP-PLZF was not changed between before and after the TPA treatment. On the other hand, in HT1080/ΔMP-ADAM12/HB-EGF, the TPA treatment did not trigger processing. In HT1080/HB-EGF-UC, since HB-EGF is resistant against processing, the fluorescence intensity of CFP-PLZF also was not changed in these cells between before and after the TPA treatment.

TEST EXAMPLE 4

Expression of Cyclin A in Response to the Nuclear Export of PLZF Protein

1. Test Method
Expression of cyclin A in response to the nuclear export of PLZF protein was traced by immunofluorescence. cDNA of a synthetic octapeptide (sold under the trademark FLAG by Sigma-Aldrich Co. of Missouri, USA) having high antigenicity was bound to the N terminal of the cDNA of the PLZF protein, and the cDNA of the PLZF protein was transfected into HT1080/HB-EGF using a commercially available vector (pcDNA3. 1/Hygro(+) ;Invitrogen).

The cultured transfectant was subjected to a TPA treatment (100 nM, 8 hours), and then washed with phosphate-buffered saline (PBS) and immobilized with 4% paraformaldehyde (PFA)/PBS (4° C., 10 min). Subsequently, the transfectant was treated with 0.5% triton X-100/PBS and 1% bovine serum albumin (BSA).

A mouse monoclonal IgG antibody against the transfected octapeptide and a rabbit polyclonal antibody against cyclin A were added, and incubated for one hour and the resultant was washed with PBS. Then, rhodamine-conjugated goat anti-mouse IgG antibody and a fluorescence-tagged (trademark: Alexa Fluor 488, Molecular Probes Co.) goat anti-rabbit IgG antibody were added thereto, followed by further one hour incubation. The resultant was washed with PBS, and thereafter the cells were mounted with PBS containing 5000 glycerol and 0.1% phenylene diamine and observed with a fluorescence microscope, and then the fluorescence intensity was measured with image processing software sold under the trademark LUMINA VISION by Mitani Corporation of Japan).

Figure 2:
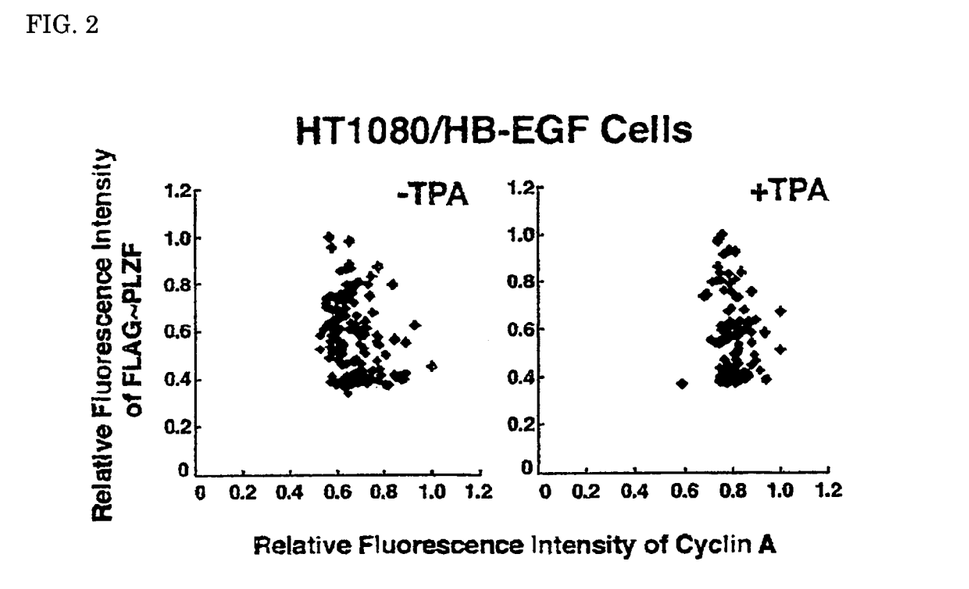
FIG. 2 shows graphs representing the effect of the nuclear export of the intranuclear PLZF protein by processing on the expression of intranuclear cyclin A. The vertical axis shows the fluorescence intensity of the fluorescence-tagged PLZF protein, and the horizontal axis shows the fluorescence intensity of cyclin A.

2. Test Results
Regarding the nucleus of each cell used in the test, the difference between the presence and the absence of the TPA treatment was evaluated with the vertical axis showing the fluorescence intensity derived from octapeptide bound to the PLZF protein, and the horizontal axis showing the fluorescence intensity derived from cyclin A (FIG. 2). It was observed that the expression of cyclin A in the nucleus that had been suppressed by the transfection of the octapeptide-tagged PLZF protein was liberated from the suppression, as a result of the nuclear export of the PLZF protein due to the TPA treatment, and the fluorescence intensity of cyclin A converged in a high intensity region (in the vicinity of 0.8).

Such an effect was not seen in HT1080/ΔMP-ADAM12/HB-EGF or HT1080/HB-EGF-UC.

TEST EXAMPLE 5

Change in the Amount of BrdU Internalized by Processing

1. Test Method

A synthetic octapeptide-tagged PLZF protein (see Test Example 4) was transfected to each of the cell groups (HT1080, HT1080/HB-EGF, HT1080/ΔMP-ADAM12/HB-EGF and HT1080/HB-EGF-UC) of Test Example 3.

Each transfectant was cultured in an eagle MEM medium (containing 3% FCS) for 36 hours, and incubated in the same medium (containing 10% FCS) for 12 hours. Thereafter, 100 nM TPA was added thereto and a treatment was performed for 2 hours. Then, 3 μg/ml of BrdU was added to the medium, followed by further two hours incubation. After immobilization with 4% PFA/PBS and permeation with 0.5% tritonX-100/PBS, the cells were treated with 2N hydrochloric acid for 30 min and subsequently with 1% BSA for 30 min.

A mouse monoclonal IgG antibody (Shigma) against the octapeptide portion and a rat monoclonal IgG antibody (Abeam Ltd.) against BrdU were added, and the resultant was incubated for one hour and washed with PBS. Then, isothiocyanate-conjugated goat anti-mouse IgG antibody and a rhodamine-conjugated goat anti-rat IgG antibody (sold by CHEMICON international Inc. of California, USA) were added thereto, followed by further incubation. The resultant was washed with PBS, and thereafter the cells were mounted with PBS containing 50% glycerol and 0.1% phenylene diamine and observed with a fluorescence microscope.

Regarding the octapeptide-tagged PLZF protein transfectants and non-transfectants, the ratios in the number of cells internalizing BrdU were compared in the presence and the absence of the TPA treatment.

2. Test Results

Figure 3:
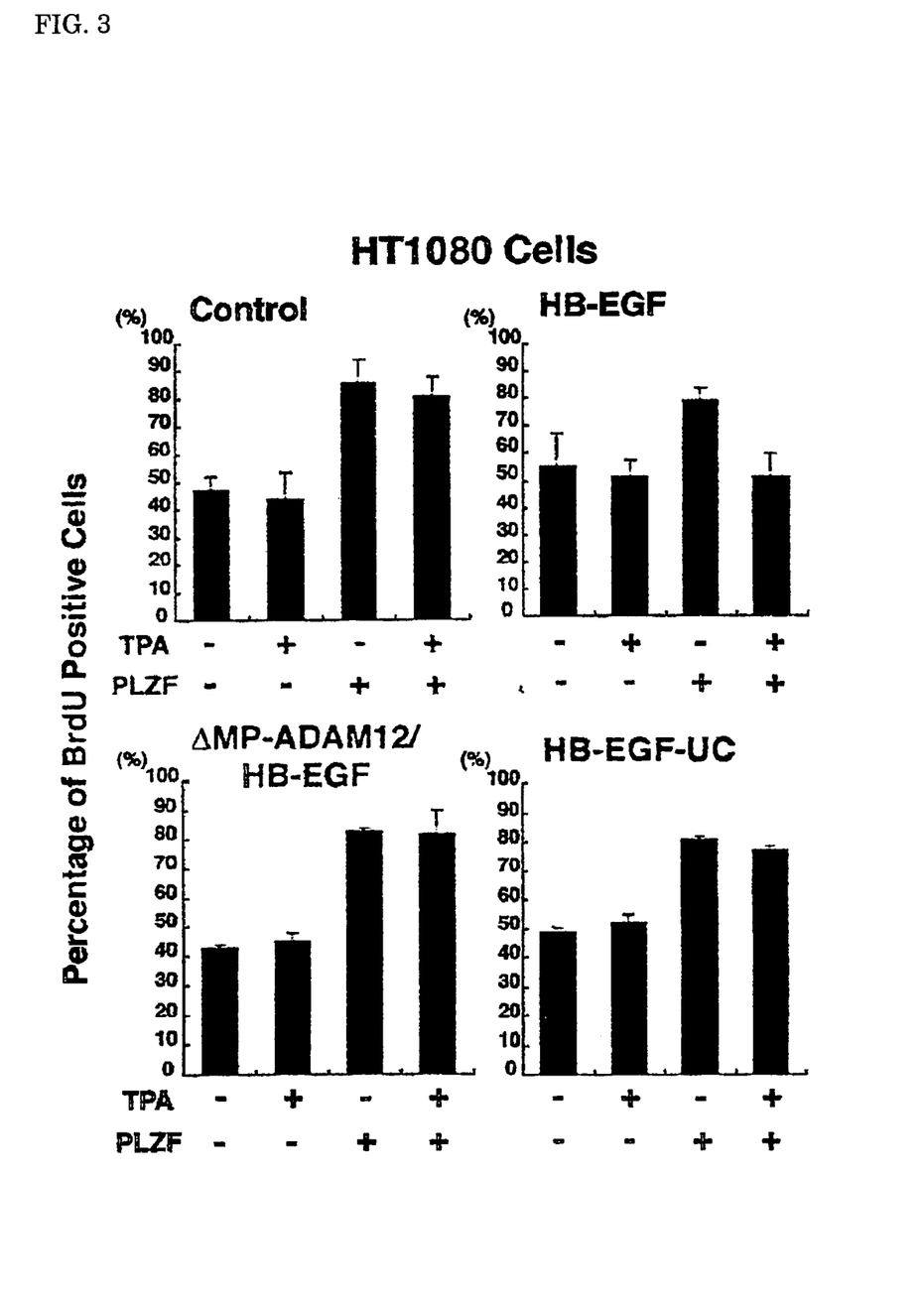
FIG. 3 shows graphs representing the effect of processing on the amount of BrdU internalized through the nuclear export of the intranuclear PLZF protein and the activation of the intranuclear cyclin A. (±) in TPA in the horizontal axis shows whether or not TPA treatment is performed, and (±) in PLZF protein shows the tagged PLZF protein transfectant/non-transfectant, respectively. The vertical axis shows the ratio (%) of the number of BrdU-internalized cells compared to the number of the transfectant or non-transfectant cells that are subjected to the test.

FIG. 3 shows the results. The internalization ratio of BrdU in the non-transfectants of the PLZF protein is generally about 40 to 50%, and there was no change with the TPA treatment. However, in PLZF transfectants, the action of cyclin A was suppressed by the suppressor effect of the expressed PLZF protein, and the cell cycle did not proceed further than the S-phase (DNA synthetic-phase), and thus the internalization ratio of BrdU was increased. In this case, when the TPA treatment was performed, the nuclear export of the PLZF protein was caused, so that the suppressor effect of this protein was weakened. Thus, cyclin A was activated and the cell cycle proceeded further onto the G1-phase from the S-phase. Consequently, the internalization ratio of BrdU decreased. However, in HT 1080 in which almost no HB-EGF was present, HT1080/ΔMP-ADAM12/HB-EGF in which processing is not caused, and HT1080/HB-EGF-UC in which processing is resisted, the TPA treatment did not change the internalization ratio of BrdU.

TEST EXAMPLE 6

Nuclear Export of Bcl-6 Protein or Myoneurin Protein by Processing

1. Test Method

Whether or not the nuclear export of transcriptional regulators occurred was examined in the same manner as in Test Example 3, except that the following cell groups were used, and Bcl-6 protein or myoneurin protein were used as the tagged transcriptional regulators, instead of the PLZF protein.

1) Human fibrosarcoma HT1080 cells
2) HT1080 cells to which HB-EGF has been transfected (HT1080/HB-EGF)

2. Test Results

Figure 4:
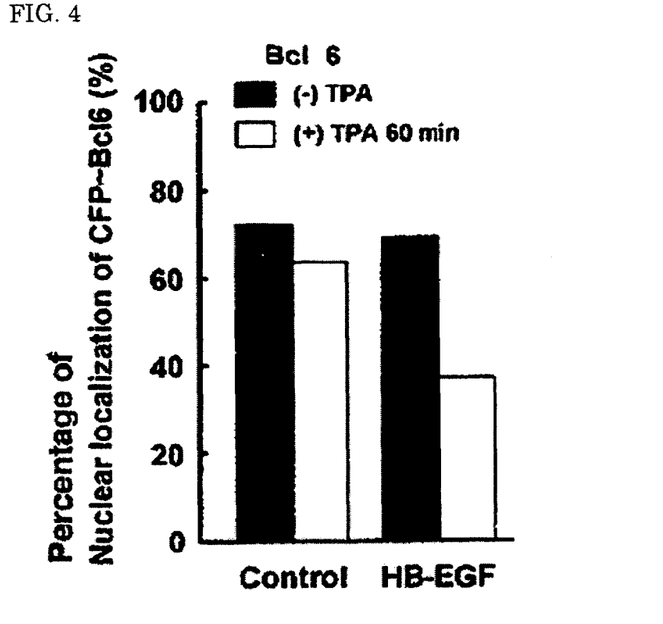
FIG. 4 is a graph showing the nuclear export effect of Bcl-6 protein by processing. The vertical axis shows the ratio (%) of the number of cells expressing CFP-Bcl-6 in the nucleus compared to the total number of the CFP-Bcl-6 transfectant cells. The colored bar graph shows the results without TPA treatment, and the colorless bar graph shows the results with TPA treatment. The horizontal axis shows HB1080 and HB1080/HB-EGF respectively.
Figure 5:
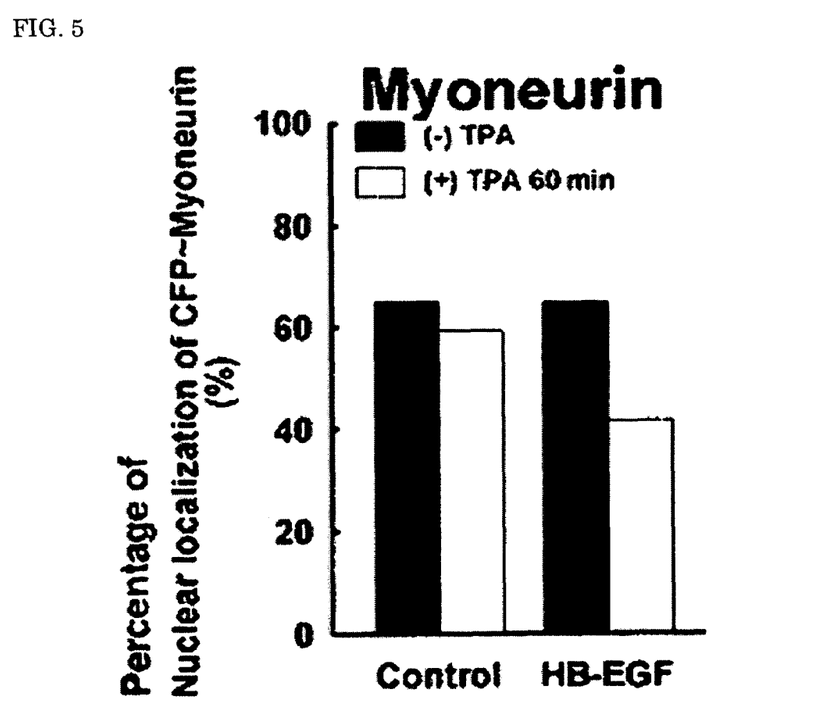
FIG. 5 is a graph showing the nuclear export effect of myoneurin protein by processing. The vertical axis shows the ratio (%) of the number of cells expressing CFP-myoneurin in the nucleus compared to the total number of the CFP-myoneurin transfectant cells. The colored bar graph shows the results without TPA treatment, and the colorless bar graph shows the results with TPA treatment. The horizontal axis shows HB1080 and HB1080/HB-EGF respectively.

FIGS. 4 and 5 show the results. Processing was triggered by the TPA treatment, and the remaining fragment of HB-EGF caused the nuclear export of the Bcl-6 protein or the myoneurin protein present in the nucleus in a cell. As a result, in the HT1080/HB-EGF, the fluorescence intensity of CFP-Bcl-6 or CFP-myoneurin present in the nucleus was decreased by the TPA treatment.

TEST EXAMPLE 7

Nuclear Export of KIAA0441 Protein by Processing

1. Test Method

Whether or not the nuclear export of transcriptional regulators occurred was examined in the same manner as in Test Example 3, except that the following cell groups were used, KIAA0441 protein was used as the tagged transcriptional regulator, instead of the PLZF protein, and epiregulin (ER) was used, instead of HB-EGF.

1) Human fibrosarcoma HT1080 cells
2) HT1080 cells to which epiregulin has been transfected (HT1080/ER)

2. Test Results

Figure 6:
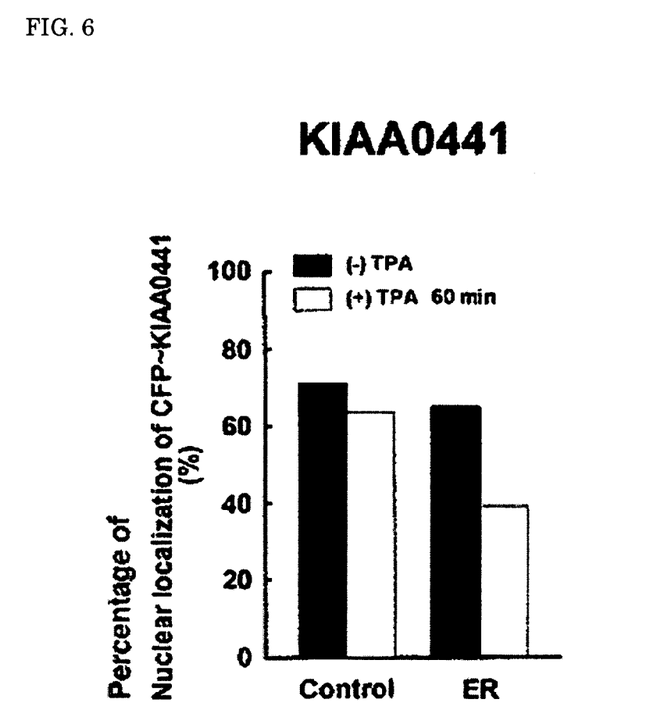
FIG. 6 is a graph showing the nuclear export effect of KIAA0441 protein. The vertical axis shows the ratio (%) of the number of cells expressing CFP-KIAA0441 in the nucleus compared to the total number of the CFP-KIAA0441 transfectant cells. The colored bar graph shows the results without TPA treatment, and the colorless bar graph shows the results with TPA treatment. The horizontal axis shows HB1080 and HB1080/ER respectively.

FIG. 6 shows the results. Processing was triggered by the TPA treatment, and the remaining fragment of epiregulin caused the nuclear export of KIAA0441 protein present in the nucleus in a cell. As a result, in the HT1080/ER, the fluorescence intensity of CFP-KIAA0441 present in the nucleus was decreased by the TPA treatment.

EXAMPLE

Hereinafter, the present invention will be described more specifically by way of an example.

Inhibitory Effect of Reptomycin B Against the Nuclear Export of the PLZF Protein 1. A compound to be tested reptomycin B (LMB)
2. Test method HT1080/HB-EGF to which CFP-PLZF had been transfected (see Test Example 3) was cultured for 24 hours, and then treated with 100 nM TPA in the copresence of LMB (10 ng/ml) for 60 min. The number of the cells expressing CFP-PLZF in the nucleus was measured with a microscope before and after the TPA treatment and the ratio was calculated.

As the control, the ratio of the number of the cells expressing CFP-PLZF before and after the TPA treatment when the TPA treatment was performed without adding LMB was obtained, and compared with the ratio when LMB was added. Thus, the compound LMB to be tested was evaluated.

3. Test Results

Figure 7:
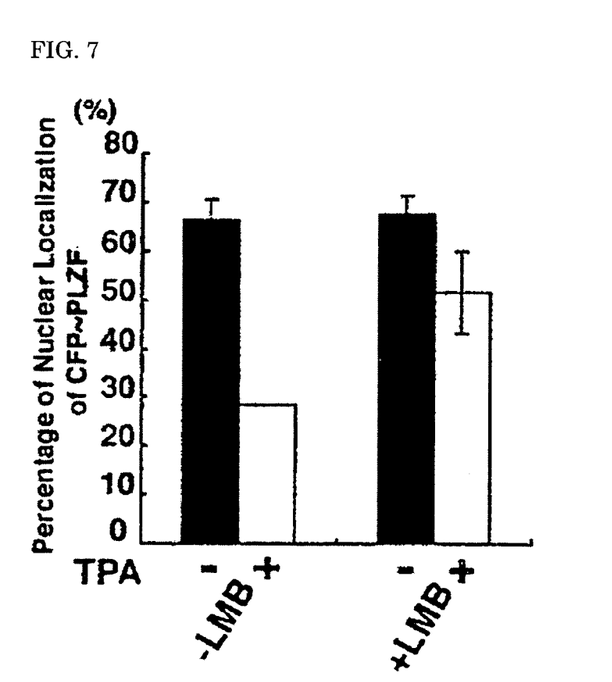
FIG. 7 shows a graph representing the inhibitory effect of reptomycin B on the nuclear export of the PLZF protein by processing. The vertical axis shows the ratio (%) of the number of cells expressing CFP-PLZF in the nucleus compared to the total number of the CFP-PLZF transfectant cells. (±) in TPA in the horizontal axis shows whether or not TPA treatment is performed, and (±) in LMB shows the presence or the absence of reptomycin B, which is a compound to be tested, respectively.

FIG. 7 shows the numbers of the cells expressing CFP-PLZF in the nucleus before and after the TPA treatment with and without LMB. It was confirmed that LMB inhibited the nuclear export of the PLZF protein.

INDUSTRIAL APPLICABILITY

When in cells transfected with amino-terminally (N terminally) fluorescence-tagged CFP-PLZF, the extracellular domain of HB-EGF was subjected to processing by a solubilizing enzyme, the nuclear export of the tagged PLZF protein was observed, and this effect was suppressed by a processing inhibitor (Test Example 3).

Next, it was confirmed that PLZF proteins and cyclin A were confirmed to be present in the nucleus by immunofluorescence, and thereafter when the extracellular domain of HB-EGF was subjected to processing by a solubilizing enzyme, the nuclear export of the PLZF protein occurred and the fluorescence intensity of cyclin A was increased (Test Example 4).

When the PLZF protein is forcefully expressed in cells, the action of cyclin A is suppressed and the cells concentrate on the S-phase of the cell cycle, so that the amount of internalized bromodeoxyuridine (BrdU) temporarily increases. At this point, when the extracellular domain is subjected to processing by a solubilizing enzyme, the action of cyclin A is accelerated by the nuclear export of the PLZF protein, and the cell growth proceeds from the S-phase to the G2-phase, and thus the amount of internalized BrdU decreases (Test Example 5).

It was confirmed that even after the processing of the extracellular domain by a solubilizing enzyme occurred, the addition of reptomycin B actually inhibits the nuclear export of the PLZF protein (see the example). Since reptomycin B is known as an inhibitor of nuclear export (Kudo et al., Proc. Natl. Acad. Sci. USA, 96,9112-9117(1999)) and an antitumor antibiotic, the essence of the antitumor action is to inhibit the nuclear export of intranuclear transcriptional regulator by intracellular domain, and thus it was confirmed that the present invention is useful as a method for screening a cytostatic agent.

Therefore, the screening method of the present invention can be performed as primary screening for a cytostatic agent that can inhibit the intracellular signaling process and also can be performed as secondary screening (confirmation test) to confirm the cytostatic ability (antitumor action) of a substance to be tested. Furthermore, the cytostatic agent obtained by the production method of the present invention is very useful as an antitumor agent, an antirheumatic agent, an agent for treating cardiac disorder, etc. that are based on a novel action mechanism.

The invention claimed is:

1. A method for screening a cytostatic agent comprising the steps of:
   producing within a cell at least one of (A) a remaining fragment of HB-EGF, and (B) a modified remaining fragment of HB-EGF;
   determining at least one of (i) an extent of export from the nucleus of the cell of a tagged-PLZF protein to which any of (A) and (B) is bound, and (ii) an extent of signalling from the remaining fragment to a PLZF protein,
   wherein the production and determination steps are conducted for each of the cases in the presence and in the absence of a candidate substance to be tested;
   correlating at least one of (i) a reduced extent of the export from the nucleus and (ii) an inhibited signalling when the candidate substance is present, as compared to when it is absent, with a cytostatic property of the candidate substance,
   wherein the modified remaining fragment (B) is a remaining fragment of HB-EGF in which ten of the amino acids at the C-terminal of HB-EGF have been deleted.

2. The method for screening a cytostatic agent according to claim 1, wherein the production step is a step of producing a remaining fragment of HB-EGF by processing of the growth factor; and the determination step is a step of determining an extent of export from the nucleus of a tagged PLZF protein.

3. The method for screening a cytostatic agent according to claim 1, wherein the production step is a step of producing a tagged remaining fragment of HB-EGF by processing of the growth factor; and the determination step is a step of determining an effect of inhibiting signaling from the tagged remaining fragment to a PLZF protein.

4. The method for screening a cytostatic agent according to claim 3, wherein the signaling from the tagged remaining fragment to a PLZF protein in the determination step is signaling mediated by a Zn finger region of the PLZF protein.

5. The method for screening a cytostatic agent according to claim 4, wherein the Zn finger region is a region having Zn5 to Zn8 region of a PLZF protein.

6. The method for screening a cytostatic agent according to any one of claims 3 to 5, wherein the signaling from the tagged remaining fragment to the PLZF protein in the determination step is signaling mediated by the following portion (iv) of the tagged remaining fragment, wherein (iv) is an amino acid sequence portion corresponding to the $185^{th}$ to $198^{th}$ amino acids (SEQ ID NO:4) from an amino terminal in the HB-EGF before processing.

7. The method for screening a cytostatic agent according to claim 2 or 3, wherein production of the remaining fragment or the tagged remaining fragment in the production step is confirmed by detection of the solubilized HB-EGF.

8. The method for screening a cytostatic agent according to any one of claims 2 to 5, wherein at least one of a fluorescent tag and a peptide having antigenicity is used to tag or label the PLZF protein.

9. The method for screening a cytostatic agent according to claim 8, wherein a fluorescent protein selected from the group consisting of a cyan fluorescent protein (CFP), a yellow fluorescent protein (YFP), and a green fluorescent protein (GFP) is used to tag or label the PLZF protein.

10. A method for screening a cytostatic agent comprising the steps of:
    producing within a cell (a remaining fragment of HB-LGF;
    determining at least one of (i) an extent of export from the nucleus of the cell of a tagged-PLZF protein to which the remaining fragment of HB-LGF is bound, and (ii) an extent of signalling from the remaining fragment to a PLZF protein,
    wherein the production and determination steps are conducted for each of the cases in the presence and in the absence of a candidate substance to be tested;
    correlating at least one of U) a reduced extent of the export from the nucleus and (ii) an inhibited signalling when the candidate substance is present, as compared to when it is absent, with a cytostatic property of the candidate substance.

* * * * *

UNITED STATES PATENT AND TRADEMARK OFFICE
CERTIFICATE OF CORRECTION

PATENT NO.        : 7,498,127 B2
APPLICATION NO.   : 10/506049
DATED             : March 3, 2009
INVENTOR(S)       : Shigeki Higashiyama et al.

It is certified that error appears in the above-identified patent and that said Letters Patent is hereby corrected as shown below:

In the Claims:

Change Claims 1 to 10, col. 17, line 14 to col. 18, line 49, to be

-- 1.
A method for screening a cytostatic agent comprising the steps of:
- producing within a cell at least one of (A) a remaining fragment of HB-EGF, (B) a modified remaining fragment of HB-EGF, or (C) a tagged remaining fragment of (A) or (B);
- determining at least one of (i) an extent of export from the nucleus of the cell of a tagged PLZF protein to which any of (A), (B), or (C) is bound, and (ii) an extent of intracellular secondary messenger signaling from the remaining fragment of HB-EGF to a PLZF protein, wherein the production and determination steps are conducted for each of the screenings in the presence and in the absence of a candidate substance to be tested;
- correlating at least one of (i) a reduced extent of the export of the bound and tagged PLZF protein from the nucleus, and (ii) inhibited intracellular secondary messenger signaling when the candidate substance is present, as compared to when it is absent, with a cytostatic property of the candidate substance; wherein the modified remaining fragment (B) is a remaining fragment of HB-EGF in which the last ten amino acids at the C-terminal of HB-EGF, corresponding with residues 199-208 of full-length HB-EGF, have been deleted.

UNITED STATES PATENT AND TRADEMARK OFFICE
CERTIFICATE OF CORRECTION

| | |
|---|---|
| PATENT NO. | : 7,498,127 B2 |
| APPLICATION NO. | : 10/506049 |
| DATED | : March 3, 2009 |
| INVENTOR(S) | : Shigeki Higashiyama et al. |

It is certified that error appears in the above-identified patent and that said Letters Patent is hereby corrected as shown below:

2.
   The method for screening a cytostatic agent according to claim 1, wherein the production step is a step of producing a remaining fragment of HB-EGF by proteolytic processing of the growth factor; and the determination step is a step of determining an extent of export from the nucleus of a tagged PLZF protein.

3.
   The method for screening a cytostatic agent according to claim 1, wherein the production step comprises producing a tagged remaining fragment of HB-EGF by proteolytic processing of the growth factor, and the determination step comprises determining an effect of inhibiting intracellular secondary messenger signaling from the tagged remaining fragment of HB-EGF to a PLZF protein.

4.
   The method for screening a cytostatic agent according to claim 3, wherein the intracellular secondary messenger signaling from the tagged remaining fragment of HB-EGF to a PLZF protein in the determination step is intracellular secondary messenger signaling mediated by a Zn finger region of the PLZF protein.

5.
   The method for screening a cytostatic agent according to claim 4, wherein the Zn finger region is a region comprising a Zn5 to Zn8 region of a PLZF protein.

UNITED STATES PATENT AND TRADEMARK OFFICE
CERTIFICATE OF CORRECTION

PATENT NO. : 7,498,127 B2
APPLICATION NO. : 10/506049
DATED : March 3, 2009
INVENTOR(S) : Shigeki Higashiyama et al.

It is certified that error appears in the above-identified patent and that said Letters Patent is hereby corrected as shown below:

6. The method for screening a cytostatic agent according to any one of claims 3 to 5, wherein the intracellular secondary messenger signaling from the tagged remaining fragment of HB-EGF to the PLZF protein in the determination step is signaling mediated by the following portion (iv) of the tagged remaining fragment, wherein (iv) is the polypeptide sequence consisting of SEQ ID NO: 4, which corresponds with residues 185-198 of full-length HB-EGF.

7. The method for screening a cytostatic agent according to claim 2 or 3, wherein the production step is confirmed by detection of the solubilized HB-EGF.

8. The method for screening a cytostatic agent according to any one of claims 2 to 5, wherein at least one of a fluorescent protein and a peptide having antigenicity is used to tag the PLZF protein.

9. The method for screening a cytostatic agent according to claim 10, wherein the fluorescent protein selected from the group consisting of a cyan fluorescent protein (CFP), a yellow fluorescent protein (YFP), and a green fluorescent protein (GFP) is used to tag the PLZF protein.

UNITED STATES PATENT AND TRADEMARK OFFICE
CERTIFICATE OF CORRECTION

PATENT NO. : 7,498,127 B2
APPLICATION NO. : 10/506049
DATED : March 3, 2009
INVENTOR(S) : Shigeki Higashiyama et al.

It is certified that error appears in the above-identified patent and that said Letters Patent is hereby corrected as shown below:

10.
        A method for screening a cytostatic agent comprising the steps of:
        - producing within a cell a remaining fragment of HB-EGF;
        - determining at least one of (i) an extent of export from the nucleus of the cell of a tagged PLZF protein to which the remaining fragment of HB-EGF is bound, and (ii) an extent of intracellular secondary messenger signaling from the remaining fragment of HB-EGF to a PLZF protein,
wherein the production and determination steps are conducted for each screening in the presence and in the absence of a candidate substance to be tested;
- correlating at least one of (i) a reduced extent of the export from the nucleus of the bound, tagged PLZF protein and (ii) inhibited intracellular secondary messenger signaling, when the candidate substance is present, as compared to when it is absent, with a cytostatic property of the candidate substance. --

Signed and Sealed this

Second Day of June, 2009

JOHN DOLL
*Acting Director of the United States Patent and Trademark Office*

SEQUENCE LISTING

```
<160> NUMBER OF SEQ ID NOS: 5

<210> SEQ ID NO 1
<211> LENGTH: 24
<212> TYPE: PRT
<213> ORGANISM: Homo sapiens

<400> SEQUENCE: 1

Arg Tyr His Arg Arg Gly Gly Tyr Asp Val Glu Asn Glu Glu Lys Val
1               5                   10                  15

Lys Leu Gly Met Thr Asn Ser His
            20

<210> SEQ ID NO 2
<211> LENGTH: 6
<212> TYPE: PRT
<213> ORGANISM: Homo sapiens

<400> SEQUENCE: 2

Thr Gly Glu Lys Pro Tyr
1               5

<210> SEQ ID NO 3
<211> LENGTH: 7
<212> TYPE: PRT
<213> ORGANISM: Homo sapiens

<400> SEQUENCE: 3

Thr Gly Glu Lys Pro Tyr Pro
1               5

<210> SEQ ID NO 4
<211> LENGTH: 14
<212> TYPE: PRT
<213> ORGANISM: Homo sapiens

<400> SEQUENCE: 4

Arg Tyr His Arg Arg Gly Gly Tyr Asp Val Glu Asn Glu Glu
1               5                   10
```

```
<210> SEQ ID NO 5
<211> LENGTH: 10
<212> TYPE: PRT
<213> ORGANISM: Homo sapiens

<400> SEQUENCE: 5

Lys Val Lys Leu Gly Met Thr Asn Ser His
1               5                   10
```